US00PP27752P3

(12) United States Plant Patent
Suzuki

(10) Patent No.: US PP27,752 P3
(45) Date of Patent: Mar. 7, 2017

(54) ***LOROPETALUM* PLANT NAMED 'BENI HIME'**

(50) Latin Name: *Loropetalum chinense*
Varietal Denomination: BENI HIME

(71) Applicant: Yuji Suzuki, Kawaguchi (JP)

(72) Inventor: Yuji Suzuki, Kawaguchi (JP)

(73) Assignee: Spring Meadow Nursery Inc., Grand Haven, MI (US)

( * ) Notice: Subject to any disclaimer, the term of this patent is extended or adjusted under 35 U.S.C. 154(b) by 83 days.

(21) Appl. No.: 14/544,873

(22) Filed: Feb. 26, 2015

(65) Prior Publication Data

US 2016/0262297 P1 Sep. 8, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Loropetalum* cultivar named 'BENI HIME' is disclosed, characterized by very small, glossy deep red/maroon foliage that holds its color well all season. Plant habit is completely prostrate with no mounding. The new variety is a *Loropetalum*, normally produced as an outdoor garden or container plant.

1 Drawing Sheet

Latin name of the genus and species: *Loropetalum chinense.*

Variety denomination: 'BENI HIME'.

BACKGROUND OF THE INVENTION

The new *Loropetalum* cultivar is a product of a planned breeding program conducted by the inventor, Yuji Suzuki, in Kawaguchi City, Saitama, Japan. The objective of the breeding program was to produce new *Loropetalum* varieties with better foliage color and improved flowering for ornamental commercial applications. The cross resulting in this new variety was made during Apr. 2, 2006.

The seed parent is the commercial variety referred to as *Loropetalum* 'Kurobijin' U.S. Plant Pat. No. 23,176. The pollen parent is the unpatented, propriety variety referred to as *Loropetalum* '5-17'. The new variety was selected by the inventor in a group of seedlings resulting from the 2006 crossing, in a nursery in Kawaguchi City, Saitama, Japan.

Asexual reproduction of the new cultivar was performed by softwood cuttings. This was first performed at a nursery in Kawaguchi City, Saitama, Japan, in 2011 and has shown that the unique features of this cultivar are stable and reproduced true to type in 5 successive generations.

SUMMARY OF THE INVENTION

The cultivar 'BENI HIME' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BENI HIME' These characteristics in combination distinguish 'BENI HIME' as a new and distinct *Loropetalum* cultivar:

1. Very small, rounded deep red/maroon foliage that holds its color extremely well all season.
2. Extremely prostrate growing, no mounding
3. Glossy foliage.

Plants of the new cultivar 'BENI HIME' are similar to plants of the seed parent, *Loropetalum* 'Kurobijin' in most horticultural characteristics, however, plants of the new cultivar 'BENI HIME' differ in the following;

1. Magenta/pink flower color of the new variety. The parent flower color is darker red.
2. Back side of leaves is grayish green. The parent's leaves are red on back side
3. Very small ovate leaves. The parent's leaves are ovate and larger.
4. Spreading and very prostrate growth habit. The parent growth habit is spreading but not as prostrate.
5. Dark red foliage. The parent's foliage is black.

Plants of the new cultivar 'BENI HIME' are similar to plants of the pollen parent, *Loropetalum* '5-17' in most horticultural characteristics, however, plants of the new cultivar 'BENI HIME' differ in the following;

1. Magenta/pink flowers. The parent flower color is darker red.
2. Back side of leaves is grayish green. The pollen parent leaves are red on back side.
3. Very small ovate leaves. The parent's leaves are ovate and larger.
4. Spreading and very prostrate growth habit. The parent growth habit is spreading but not as prostrate.
5. Foliage holds color better all season.

COMMERCIAL COMPARISON

Plants of the new cultivar 'BENI HIME' are comparable to the patented, commercial variety *Loropetalum* 'Peack' U.S. Plant Pat. No. 18,441. The two *Loropetalum* varieties are similar in most horticultural characteristics; however, the new variety 'BENI HIME' differs in the following:

1. Very prostrate and spreading growth habit. The comparator growth habit is mounding.
2. Much smaller leaves.
3. Very low growing 10-12 inches. The comparator is slightly taller 1-2 feet.

BRIEF DESCRIPTION OF THE PHOTOGRAPH

The accompanying photograph in FIG. 1 illustrates in full color a typical plant of 'BENI HIME' grown in a 1 gallon pot. Age of the plant photographed is approximately 1 to 2 years old from a rooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BENI HIME' plants grown in a greenhouse, in Grand Haven Mich. The growing temperature averaged from 60-65° F. during the day and from 40-50° F. during the night. Growing conditions are double poly from Fall through Winter heated to 35° F. The poly was removed in the Spring. Shade cloth was used through the Summer. Measurements and numerical values represent averages of typical plant types.

Botanical classification: *Loropetalum* 'BENI HIME'.

PROPAGATION:

Type of propagation typically used: Cutting.
Time to initiate roots: 18 days at 27° C.
Number of days to produce a rooted liner in summer: 110 days at 27° C.
Root description: Medium to thick, fibrous, free branching and fleshy. New roots are purple in color, aging to brown.

PLANT

Type of plant: Perennial shrub.
Age of plant described: Approximately 2 years old.
Container size of the plant described: #1.
Growth habit: Prostrate.
Height: 25 cm.
Plant spread: Approximately 90 cm.
Growth rate: Moderate.
Plant vigor: Good, no problems in production observed.
Branching characteristics: Lateral, basal branching.
Characteristics of primary lateral branches:
- *Length.*—28 cm.
- *Quantity:* 24.
- *Diameter.*—2.5 mm.
- *Color.*—Young stems: Near RHS Greyed-purple 187B. Older stems: Near RHS Brown 200C.
- *Aspect.*—0-20° from center of plant.
- *Strength.*—Good.

Internode length: 1.35 cm.
Note: Stem pubescence is more prevalent in younger stems.
Other plant characteristics: Very dwarf.

FOLIAGE

Leaf:
- *Arrangement.*—Alternate, single.
- *Quantity.*—Approximately 50 per branch.
- *Average length.*—1.4-3.2 cm.
- *Average width.*—1.0-2.3 cm.
- *Shape of blade.*—Ovate.
- *Apex.*—Acute.
- *Base.*—Oblique.
- *Margin.*—Entire.
- *Texture of top surface.*—Smooth and slightly rough due to presence of sparse pubescence.
- *Texture of bottom surface.*—Ribbed due to protruding veins. No pubescence on older leaves and minimal on young leaves.
- *Appearance.*—Very glossy upper surface, slightly matte lower surface.
- *Color.*—Young foliage upper side: Near RHS Greyed-purple 187A. Young foliage under side: Glaucous. Near RHS Red-purple 59A. Mature foliage upper side: Near RHS Black 202A with undertones of green and maroon. Mature foliage under side: Glaucous. Near RHS Greyed-purple 187B.
- *Venation.*—Type: Pinnate. Venation color upper side: Midribs and veins are depressed on the upper side. Color does not differ from the leaf color. Venation color under side: Midribs and veins are prominent on the underside. Near RHS Greyed-purple Group 187D.
- *Petiole.*—Length: 0.2 to 0.3 cm. Diameter: 1 mm. Color: Near RHS Greyed-purple 187B.

FLOWER

Inflorescence and flower type and habit: Terminal or axial occurring umbel.
Quantity of flowers per inflorescence: 3-6.
Flower type: Perfect, irregular configuration of strap like petals.
Flower aspect: Upright and outward.
Quantity of flowers per lateral stem: 12-28.
Quantity of flowers per plant: 60-500, depending on age.
Natural flowering season: Spring with some re-bloom late Spring to Summer.
Fragrance: None.
Bud:
- *Shape.*—Obovate.
- *Length.*—3 mm.
- *Diameter.*—2 mm.
- *Color.*—Near RHS Red-purple 61A.

Petals:
- *Quantity per flower.*—4.
- *Shape.*—Linear, not fused.
- *Margin.*—Entire.
- *Texture.*—Smooth, silky, upper and lower surfaces.
- *Appearance.*—Somewhat shiny.
- *Length.*—11 mm.
- *Width.*—2 mm.
- *Tip.*—Acute to retuse.
- *Color.*—When opening: Upper surface: Near RHS Red-purple 61A. Lower surface: Near RHS Red-purple 61B. Fully opened: Upper surface: Near RHS Red-purple 61B. Lower surface: Near RHS Red-purple 61B.

Sepals:

*Quantity per flower.*—4.

*Appearance*.—Matte.

*Texture*.—Lightly pubescent.

*Arrangement*.—Whorl.

*Shape*.—Ovate and fused, slightly curled outward.

*Length*.—3 mm.

*Width*.—2 mm.

*Tip*.—Slightly reflexed.

*Base*.—Fused.

*Margin*.—Entire, smooth.

*Color*.—Immature upper and lower side: Near RHS Red-purple 61B. Mature upper and lower side: Near RHS Red-purple 58A.

REPRODUCTIVE ORGANS

Stamens: Number: 4.
Pistil: Number: 2.

OTHER CHARACTERISTICS

Lowest temperature tolerant to: 5 to 10° F.

Disease/pest resistance: No unusual susceptibility to diseases or pests noted to date.

Fruits and seeds: Rarely observed. If produced, capsule size is approximately 9 mm long by 7 mm wide. Mature capsule colored between Greyed-Brown 199B and Greyed-Orange 174B. Very few seeds observed within capsule.

Drought tolerance: Moderate to good drought tolerance once established.

What is claimed is:

1. A new and distinct cultivar of *Loropetalum* plant named 'BENI HIME' as herein illustrated and described.

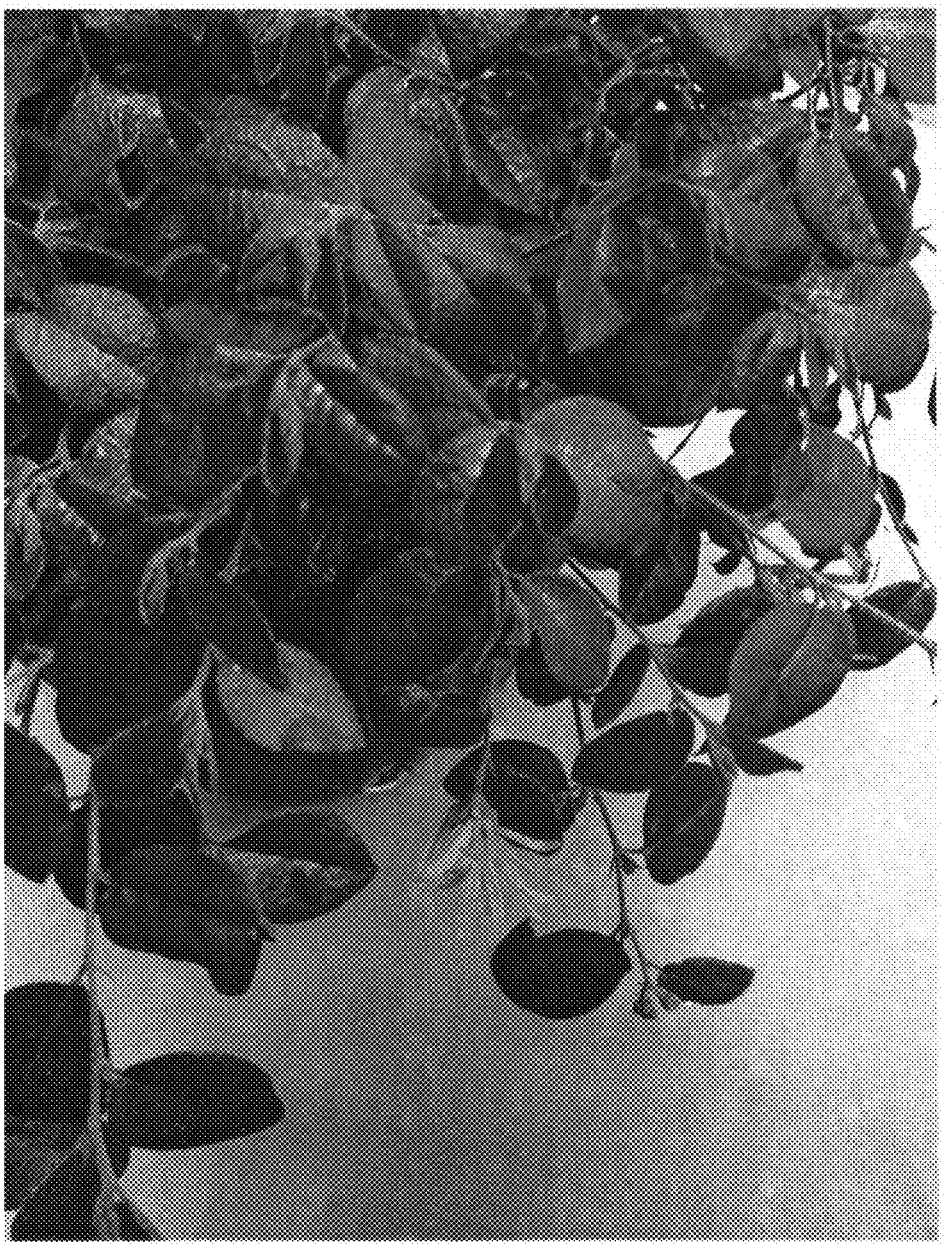

* * * * *